(12) United States Patent
Cho et al.

(10) Patent No.: US 8,414,965 B2
(45) Date of Patent: Apr. 9, 2013

(54) SUBSTRATE MANUFACTURING METHOD FOR SENSOR APPLICATIONS USING OPTICAL CHARACTERISTICS AND THE SUBSTRATE THEREFROM

(75) Inventors: Yong Jin Cho, Seoul (KR); Chul Jin Kim, Gwangju-si (KR); Chong Tai Kim, Seongnam-si (KR); Sung Wook Choi, Suwon-si (KR); Jae Ho Kim, Seongnam-si (KR); Hyo Sop Kim, Suwon-si (KR); Jin Ho Kim, Icheon-si (KR)

(73) Assignee: Korea Food Research Institute, Songnam-si, Gyeonggi-do (KR)

( * ) Notice: Subject to any disclaimer, the term of this patent is extended or adjusted under 35 U.S.C. 154(b) by 0 days.

(21) Appl. No.: 12/741,389

(22) PCT Filed: Oct. 23, 2008

(86) PCT No.: PCT/KR2008/006263
§ 371 (c)(1),
(2), (4) Date: May 5, 2010

(87) PCT Pub. No.: WO2009/075471
PCT Pub. Date: Jun. 18, 2009

(65) Prior Publication Data
US 2010/0239464 A1   Sep. 23, 2010

(30) Foreign Application Priority Data

Dec. 11, 2007   (KR) .................. 10-2007-0128476

(51) Int. Cl.
*B05D 5/12* (2006.01)
*C23C 14/28* (2006.01)
*C23C 14/30* (2006.01)
*C23C 14/14* (2006.01)
*H05B 6/00* (2006.01)
*H05B 7/00* (2006.01)
*B05D 1/18* (2006.01)
*B05D 3/00* (2006.01)

(52) U.S. Cl.
USPC ........... 427/124; 427/595; 427/596; 427/597; 427/294; 427/430.1

(58) Field of Classification Search .................. 427/124, 427/595, 596, 597, 294, 430.1
See application file for complete search history.

(56) References Cited

U.S. PATENT DOCUMENTS

| 4,996,075 A * | 2/1991 | Ogawa et al. ................. 427/457 |
| 7,202,541 B2 * | 4/2007 | Beck ............................. 257/414 |
| 2007/0235348 A1 * | 10/2007 | Nagahara et al. ............. 205/792 |

FOREIGN PATENT DOCUMENTS

| KR | 10-2004-0035206 | 4/2004 |
| KR | 10-2006-0092737 | 8/2006 |
| WO | 2005/059952 A2 | 6/2005 |

OTHER PUBLICATIONS

International Search Report dated May 12, 2009 from PCT/KR2008/006263.

*Primary Examiner* — Kelly M Gambetta
(74) *Attorney, Agent, or Firm* — Ohlandt, Greeley, Ruggiero & Perle, L.L.P.

(57) ABSTRACT

A method for manufacturing a substrate of an analytical sensor and the substrate thus prepared are disclosed. The method for manufacturing the substrate of the sensor application according to the present invention is characterized in that it comprises (a) the step of preparing a dispersed solution of nanoparticles, which are stable in a volatile organic solvent due to surface modification of nanoparticles having a pre-designed certain size on the nanometer level with an organic functional group (b) the step of preparing a single layer film of nanoparticles surface-modified with the organic functional group on the interface using said dispersed solution of nanoparticles on the basis of the Langmuir-Blodgett method, and then transferring said single layer film of nanoparticles to the substrate; and (c) the step of coating the substrate to which said single layer film of nanoparticles is transferred, with the metal thin film by means of the vacuum vapor deposition, and then optionally removing nanoparticles to manufacture a nanostructure to be used as the analytical sensor using optical characteristics. According to the method for manufacturing the substrate of the sensor application according to the present invention as above, the nanoparticles can be uniformly fixed on the solid substrate having a great area above $10 \times 10$ cm$^2$ using the Langmuir-Blodgett method, and by such method the size, distance and shape of nanoparticles can be controlled to manufacture the nanostructures to be used as the analytical sensor, which is possible to reproduce and mass-produce. When the sensitivity property of the sensor is measured using the nanostructure substrate, thus produced, to be used as the analytical sensor, it can be identified that the sensitivity can be highly improved.

13 Claims, 7 Drawing Sheets

SUBSTRATE MANUFACTURING METHOD FOR SENSOR APPLICATIONS USING OPTICAL CHARACTERISTICS AND THE SUBSTRATE THEREFROM

TECHNICAL FIELD

The present invention relates to a method for manufacturing a substrate of an analytical sensor using optical characteristics, and a substrate thus produced. More specifically, the present invention relates to a method for manufacturing a substrate of an analytical sensor using Langruir-Blodgett (LB) method, and a substrate thus produced.

BACKGROUND ART

The substrate for "the analytical sensor using optical characteristics" refers to substrates for Surface Plasmon Resonance (hereinafter referred to as "SPR"), surface-enhanced Raman scattering substrates, optical biosensor substrates, electrochemical sensor substrates, mechanical sensor substrates and SPM (Scanning Probe Microscope) sensor substrates, etc. Hereinafter, it is abbreviated to "the analytical sensor".

Among them, the surface plasmon mainly used as an analytical sensor chip is the term referring to the vibration phenomenon of electron density proceeding along with the interface between the metal thin film and the dielectric material. The surface plasmon, which is an electromagnetic wave proceeding along with the interface between the metal and the dielectric material, is not propagated inside the dielectric material but is present only on the surface since the size of wave vector thereof is greater than the vector of light proceeding inside the dielectric material. Therefore, to excite the surface plasmon it is required to make the wave vector great.

As the means for enhancing the wave vector, the attenuated total reflection method utilizing the prism with a high refractive index is used. It utilizes the prism and the metal thin film coated on the prism, wherein the metal thin film should be thin so that the incident photons into the prism can be passed through the metal thin film. The surface plasmon can be excited only when the incident photons are entered into prism through the metal thin film at an angle greater than an angle of total reflection.

All the photons greatly incident at the angle of total reflection are absorbed on the interface between the metal thin film and the dielectric material at a specific angle due to the surface plasmon resonance. The surface plasmon resonance generates a strong electric field at the interface between the metal thin film and the dielectric material, which electric field is controlled only on the surface but is perpendicularly attenuated by an exponential function. The strength of electric field in such a case has a great value ten to hundred times the strength in case where the surface plasmon is not excited.

Since the surface plasmon is greatly varied depending on the shape and reflective index of the dielectric material contiguous to the metal thin film, such properties are utilized to study the surface plasmon band gap by the interface between the dielectric material having a periodic structure and the flat metal thin film. As examples of the application thereof, the sensor using diffraction grids is intensively limited with respect to the measuring parameters, as compared to the sensor using prisms. In order to complement such limitation, it can be seen that the incidence angle may be reduced by moving the incident light in the direction of surface to gradually increase a period of the diffraction grid.

Meanwhile, the surface plasmon resonance is very sensitive to the incidence angle and therefore, can also be used in the small diffraction grid structure. It is anticipated that such study can be greatly utilized for the information storage elements or the optical sensor such as optical microscope, etc.

FIG. 1 shows the structure of general SPR systems. Referring to FIG. 1, the surface plasmon is a collective vibration phenomenon of electrons generated on the surface of the metal thin film (100), and the surface plasmon wave generated therefrom is a kind of surface electromagnetic waves proceeding along with the interface between the metal thin film (100) and the dielectric material (104) contiguous thereto. In the arrangement for surface plasmon resonance, the surface plasmon resonance is generated from a specific incidence angle at which the wave vector of the Everdesont wave conforms to the wave vector of the surface plasmon on the interface between the metal thin film (100) and the prism (102).

A change in the properties of the surface plasmon resonance according to the thickness and properties of the dielectric material on the metal thin film (100) having a nanometer thickness is utilized in the SPR sensors. Accordingly, for using the SPR sensors as a biosensor the metal thin film is coated with a physiologically active substance to induce the production of a physiological specific reaction on the metal thin film. Such metal thin film substrate coated with biological substances is designated as the SPR sensor chip. In this case, in order to improve the sensitivity of SPR sensors the metal thin films with various shapes are prepared. In the prior art, as the method for arranging the silica nanoparticles on the solid substrate the methods including spin coating, dropping method for spreading and then drying the dispersed solution, etc. have been used. However, although such prior methods can prepare the thin film by simply arranging the silica nanoparticles on the solid substrate, they have the problems that it is difficult to use them as the procedures for mass-production of the thin film with a great area within a short period, and further, to prepare the uniform substrate having a high sensitivity.

More specifically, they have the problem of a reproducibility by producing either the multi-layer film or the mono-layer film depending on various procedure conditions in manufacturing the substrate with a spin coating, for example, spin speed, time, presence of air bubbles in the dispersed solution the uniformity, and further, there are difficulties in controlling the experimental conditions each time according to the particle size and the viscosity of the solution.

According to one method using the spin coating, for example, when the nanosphere lithography masks as a polystyrene nanosphere are prepared using the spin coating method, only a part of the area of the substrate thus prepared is formed as the mono-layer film (single layer) and the remaining part of the substrate is formed as the multi-layer film (double layer). Therefore, it can be seen that it is difficult to manufacture the uniform substrate which can be produced in a large scale with a great area [John C. Hulteen, David A. Treichel, Matthew T. Smith, Michelle L. Duval, Traci R. Jensen, and Richard P. Van Duyne, "Nanosphere Lithography: Size-Tunable Silver Nanoparticle and Surface Cluster-Arrays", (J. Phys. Chem. B 1999, 103, 3854-3863)].

In case where the substrate is manufactured according to the dropping method, there are more problems as compared to the case where the spin coating method is used. Accordingly, it will be well known to a person having an ordinary knowledge in this technical field that the dropping method is substantially not utilized.

As the more effective, up-to-date method, a method, which can be said to be a confined convective assembly produced during the drying procedure has been known (Mun Ho Kim, Sang Hyuk In, and O Ok Park, "Rapid Fabrication of Two- and Three-Dimensional Colloidal Films via Confined Convective Assembly", Adv. Funct. Mater. 2005, 15, 1329-1335). This method is a method in which the dispersed solution is introduced into a gap between the substrates positioned at a certain interval, for example, at a distance of 100 μm, and a solid substrate on one side is put thereon while forming the film of particles of the dispersed solution on said substrate. However, according to this method the thickness of the film is controlled depending on a speed to raise up the substrates, a concentration of the dispersed solution, etc., but in manufacturing the single layer film there may be no room for controlling of the multi-layer film and the void as partially produced, since the film of particles is formed by a force spontaneously generated under evaporation of water. Therefore, this method also has a difficulty in forming the single layer film with a great area in a large scale.

Meanwhile, Korean Registered Patent No. 10-0597280 discloses a method for attaching the nanomaterials, wherein said nanomaterials are stably dispersed in an organic solvent, the Langmuir-Blodgett film comprising the nanomaterials is formed from the resulting dispersion, and then, the nanomaterials of said LB film are transferred and attached to the holder. In said patent, it has been described that according to the method for transferring and attaching the carbon nanotube LB film to the holder with using the Langmuir-Blodgett method (LB method) the carbon nanotube-attached nanostructures, which can be manufactured by the general semiconductor process, can be produced to allow the production of a SPM (Scanning Probe Microscope) probe capable of detecting various physical, chemical and biological signals. The Langmuir-Blodgett (LB) film refers to a thin film formed through dispersing the water-insoluble materials in the liquid phase on the water surface having a certain area, which phenomenon was first discovered by Benjamin Franklin. The principle thereof is that on the basis of the properties of the so-called amphiphilic material, i.e. the properties that one side has a hydrophobic functional group and the other side has a hydrophilic functional group, the materials are aligned in a certain orientation on the surface of water (water-air interface) to make the production of a thin film at a molecular level possible. Said registered patent attaches the carbon nanotubes to the SPM probes using such LB film However, the method for attaching the nanomaterials by using the Langmuir-Blodgett method according to said registered patent make no mention of the metal thin film to be transferred to the nanostructures which are required to be used in preparing the analytical sensor chip. In addition, there is the problem that in applying the Langmuir-Blodgett method it is difficult to transfer as the single layer the nanoparticles to be used in preparing the analytical sensor chip to the substrate. Accordingly, there remains a need for the method capable of producing the nanostructure substrate comprising the metal thin film, which can be used in preparing the analytical sensor chip, with a great area in a large scale.

DISCLOSURE OF INVENTION

Technical Problem

The present invention is to solve the above-mentioned problems involved in the prior art. Thus, the technical subject matter achieved by the present invention is to provide a method for manufacturing a substrate, which can be produced with a great area in a large scale and is used for a uniform analytical sensor, and a substrate thus produced.

Technical Solution

Although the present specification and drawings of the present are described with respect to the substrate for SPR as an example of the analytical sensor in order to more easily explain the present invention, it is obvious to a person skilled in this technical field that substrates for surface-enhanced Raman scattering substrates, optical biosensor substrates, electrochemical sensor substrates, mechanical sensor substrates and SPM (Scanning Probe Microscope) sensor substrates, etc. are also included within the scope of the present invention.

In addition, although the present invention takes silica particles as an example for forming the LB film, it is obvious to a person skilled in this technical field that particles of semiconductor materials, polymeric materials such as polystyrene, etc., various metals, e.g. gold, silver, copper, aluminum and platinum, and inorganic materials, which are used as the nanoparticles, can also be used instead of silica particles.

Furthermore, a template commonly refers to both those which are formed by removing or not removing silica particles from the substrates to which the single layer film of silica particles is transferred and the metal thin film is, in turn, formed thereon.

Further, the expression that the surface is modified with a thiol group should be understood as being that organic functional groups such as silane, amine, etc. are also included.

Finally, chloroform should be understood as being that general organic solvents are also included.

The method for manufacturing the substrate of the analytical sensor to attain the above-mentioned technical subject matters is characterized in that it comprises (a) the step of preparing a dispersed solution of nanoparticles, which arestably dispersed in a volatile organic solvent due to surface modification accomplished by fixing an organic functional group to nanoparticles (b) the step of preparing a single layer film of aligned nanoparticles having a certain structure on the water-air interface using said dispersed solution of nanoparticles on the basis of the Langmuir-Blodgett method, and then transferring said single layer film of nanoparticles to the substrate; and (c) the step of coating the substrate to which said single layer film of nanoparticles is transferred, with the metal thin film by means of the vacuum vapor deposition to form a nanostructure (nanofilm). The present method can further comprise the step of removing silica particles after coating with the metal thin film. As described above, particles of semiconductor materials, polymeric materials such as polystyrene, etc., various metals, e.g. gold, silver, copper, aluminum and platinum, and inorganic materials can be generally used as the nanoparticles. Silica particles are desirable.

The organic function groups are silane, amine and thiol groups. Thiol group is desirable.

In the present invention, the analytical sensors include surface plasmon resonance sensor, surface-enhanced Raman scattering sensor, optical biosensor, electrochemical sensor, mechanical sensor and SPM (Scanning Probe Microscope) sensor, etc. The surface plasmon resonance sensor is desirable.

The volatile organic solvents are those generally accepted by a person having an ordinary knowledge in this technical field, with chloroform being desirable.

The vacuum vapor deposition is preferably the electron-beam evaporation.

It is desirable that said metal thin film is a gold thin film.

The nanofilms produced by the method comprising the step of removing nanoparticles as shown above can be used as the template, for example, to manufacture the nanostructures (nanofilm), which can be used as the substrate for measuring the surface plasmon resonance. In addition, the nanostructures from which silica particles are not removed can be used as the template, for example, as the surface-enhanced Raman scattering substrate. The present inventors have found that the uniform substrates having a great area, for example, 10×10 cm$^2$ or more can be manufactured according to the present invention.

In addition, it is desirable that the nanoparticles in said step (a), particularly silica particles, are prepared from the self-assembling reaction of an organic molecule comprising silicon, tetraethylorthosilicate (TEOS), in the presence of ammonia water as a catalyst.

In the step (a) for preparing said silica particles, silica particles are prepared by the procedure comprising (a-1) the step of preparing silica particles by subjecting the organic molecule comprising silicon, tetraethylorthosilicate (TEOS), to the self-assembling reaction in the presence of ammonia water as a catalyst and (a-2) the step of centrifuging silica particles as prepared in said step (a-1) by means of a centrifuge for the purpose of screening only particles having a certain size, immersing, discarding the supernatant, and then drying for a baking time at a certain temperature above the phase transition temperature, and are subjected to (a-3) the step of reacting EDC (1-Ethyl-3-[3-dimethylaminopropyl] carbodiimide hydrochloride)/NHS (N-hydroxysuccinimide) materials with aminobenzothiol (ABT), as the material having an amine group and a thiol group, under ultrasound application to fix ABT on the surface of silica particles, thereby preparing the dispersed solution of ABT-fixed silica particles; and then, (a-4) are prepared as the solution to be used in the Langnuir-Blodgett method by washing the dispersed solution of ABT-fixed silica particles as prepared in said step (a-3) with ethanol and chloroform through the centrifuge procedure for the purpose of screening only particles having a certain size.

Further, it is desirable that said step (b) comprises (b-1) the step of spreading the dispersed solution of silica nanoparticles having a certain size, which are surface-modified with the organic molecule having a thiol group and dispersed in chloroform, on the water surface; (b-2) the step of placing the barrier on said water surface to gather silica particles in a certain arrangement, thereby forming the thin film; and (b-3) the step of transferring silica particles in the form of the thin film to the gold substrate in the manner that the structure and arrangement of silica particles are not changed. Silica particles of which the surface is modified with a thiol group have a hydrophobic property on one side thereof, and therefore, can form the uniform film when they are spread on the water surface. In this case, a suitable pressure applied to the barrier is 35-45 mN/m.

In addition, it is desirable that said step (c) comprises (c-1) the step of forming the flat gold substrate by the thickness on such solid substrate as a cover glass for PR by means of the vacuum vapor deposition and transferring silica particles on said substrate (c-2) the step of vapor depositing the gold thin film on the substrate with silica particles transferred thereto to a required thickness, thereby manufacturing the substrate on which the gold silica structure is formed; and (c-3) the step of optionally removing silica particles using a ultrasonic wave washer.

BEST MODE FOR CARRYING OUT THE INVENTION

Figure 1:
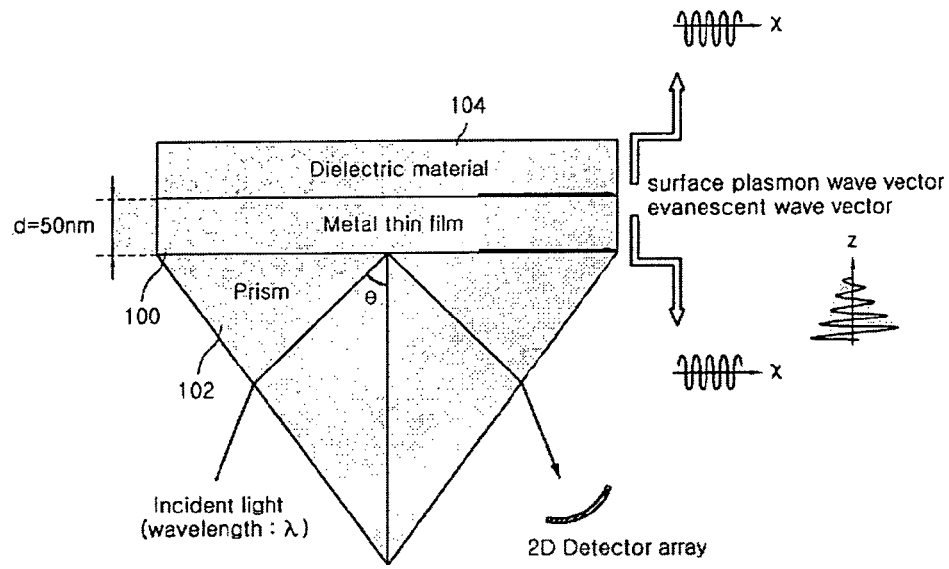
FIG. 1 is a drawing to show the structure of general SPR systems

With referring to the drawings as attached, hereinafter, the preferred examples to carry out the present invention are more specifically illustrated. The drawings as attached are intended to illustrate the invention but are not construed to limit the scope of the present invention.

In the present invention, to improve the surface plasmon resonance property silica particles are arranged on the SPR sensor chip and then, the metal thin film in which said particles have a new shape together with a good SPR sensitive property is manufactured and then, utilized as the template to produce the nanostructure.

In the process for manufacturing the substrate for measuringthe surface plasmon resonance, it has been known that the Langmuir-Blodgett method is a good method which induces the formation of a uniform single layer from the materials present on the water surface form under the condition applying the external pressure to the water surface, as described above. According to the present invention, silica particles are fixed on the substrate on the basis of such Langmuir-Blodgett method. In addition, for applying the Langmuir-Blodgett method silica particles should be dispersed in the hydrophobic and volatile organic solvents. For this purpose, the surface of silica particles is modified to be hydrophobic with a required organic functional group. The present inventors have used various organic functional groups and discovered that it is preferable to modify the particles with a thiol group having a short organic molecule.

Figure 2:
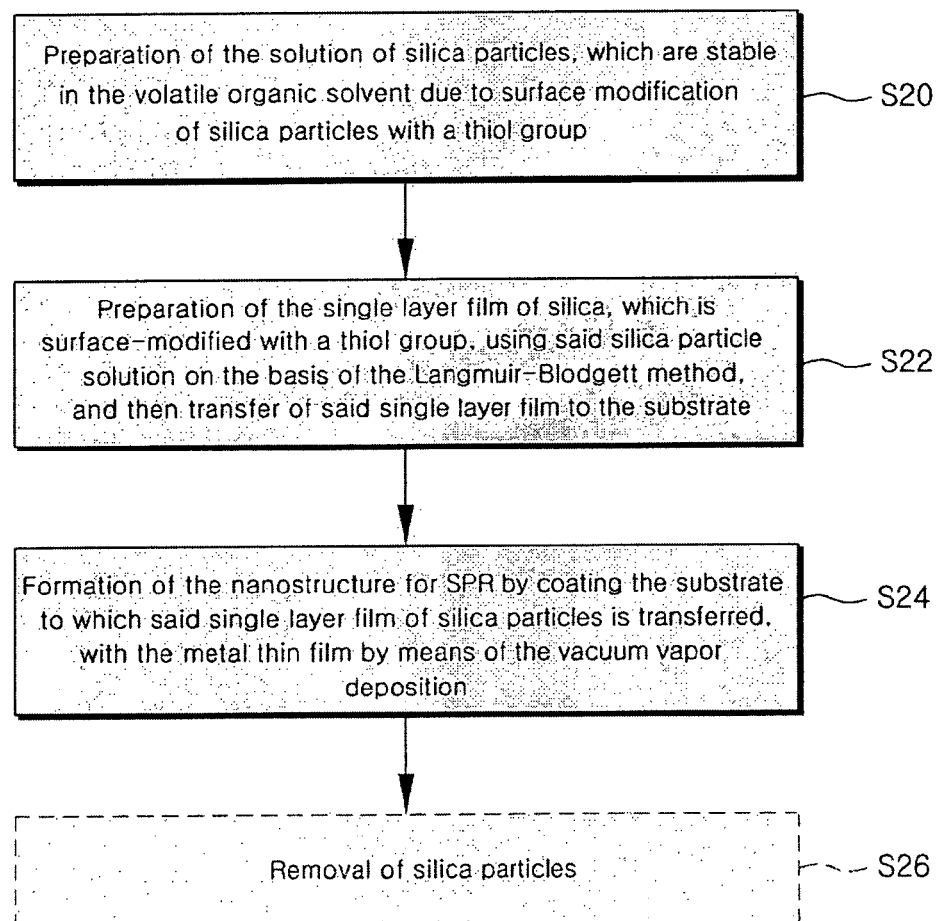
FIG. 2 is the flow chart to show the main steps of the method for manufacturing the substrate of the analytical sensor according to the preferred example of the present invention
Figure 3:
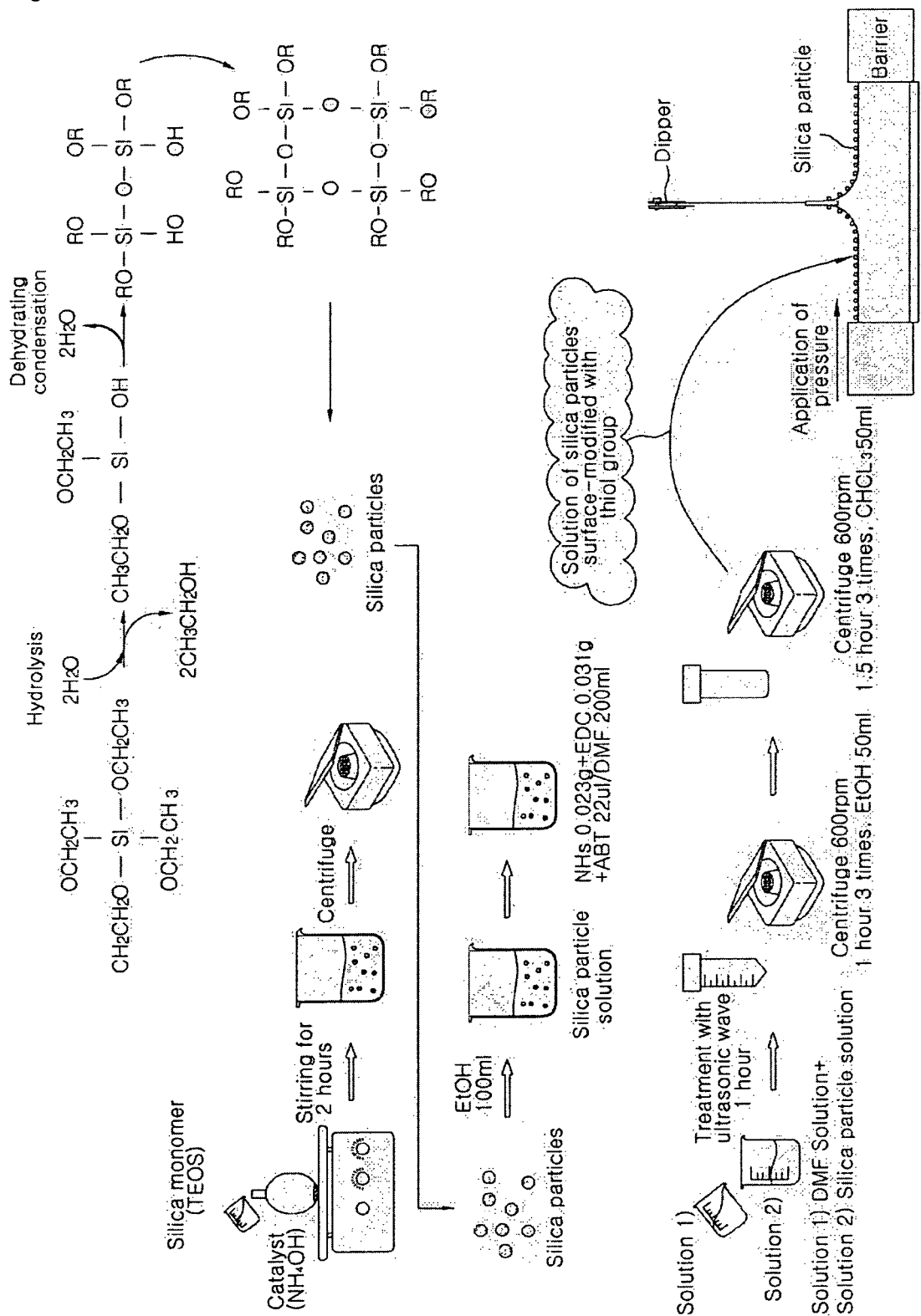
FIG. 3 is a diagram to explain the procedures of FIG. 2.

FIG. 2 shows the flow chart of the main steps of the method for manufacturing the substrate for measuring the surface plasmon resonance according to the preferred example of the present invention. FIG. 3 shows the diagram to specifically explain the procedures of FIG. 2. FIG. 2 will be frequently referred to below.

With referring to FIG. 2, in the method for manufacturing the substrate for measuring the surface plasmon resonance according to the preferred example of the present invention silica particles are first surface-modified with a thiol group to prepare the dispersed solution of silica particles stable in the organic solvent (Step S20). The method for preparing silica particles stable in the organic solvent via surface-modification with the organic functional group can be embodied as various examples, and thus, one example of the procedures of the step (S20) will be more specifically illustrated.

First, the procedure for preparing silica particles is illustrated. Ammonia water, which is the catalyst to activate tetraethylorthosilicate (TEOS) as a monomer for constitution of the structure of silica particles, is diluted with ethanol and water and then, TEOS solution is added thereto with stirring by means of an agitator. Upon stirring for a certain period, for example, for 2 hours, ethoxy groups of TEOS are activated with ammonia and water while conducting the self-assembling reaction, thereby forming silica particles. As above, it is possible to prepare silica particles from TEOS as the organic material comprising silicon, through self-assembly with using ammonia water as the catalyst. At this time, as can be seen from the following examples, the size of particles can be controlled by varying the relative concentrations of TEOS, ammonia water, etc. as used, proportions and reaction conditions.

By way of example, in order to synthesize silica particles having a size of 300 nm 1 ml of TEOS is added to the solution of 40 ml of ethanol mixed with 8.3 ml of ammonia water and 1.7 ml of distilled water in a flask with stirring, and then reacted for 2 hours. Thereafter, the reaction mixture is centrifuged to remove the impurities, and the remaining solution is dropped on the silicon wafer substrate and then, dried to confirm the size through the scanning electron microscopy (SEM).

Further, in order to synthesize silica particles having a size of 130 nm 9 ml of TEOS is added to the solution of 100 ml of ethanol mixed with 2 ml of ammonia water and 18 ml of distilled water in a flask with stirring, and then reacted for 2 hours. Thereafter, the reaction mixture is centrifuged to remove the impurities, and the remaining solution is dropped on the silicon wafer substrate and then, dried to confirm the size through the scanning electron microscopy (SEM).

Next, silica particles prepared above are centrifuged by means of a centrifuge, immersed and then, after discarding the supernatant, dried in an oven (Mitoshi) at a certain temperature above the phase transition temperature, e.g. 100° C., for a required time, e.g. for about 12 hours. In such procedures, the binding between monomers of silica particles is stabilized to secure the stability in the chemical reaction with organic solvents.

For applying the Langmuir-Blodgett method to silica particles as prepared through the above procedures, the particles should be dispersed in the phase of organic solvents. However, silica particles as prepared from the above procedures comprises many hydroxyl groups having a polar property on the surface due to TEOS, and therefore, cannot be well dispersed in the phase of organic solvents. Accordingly, it is required to conduct the step for modifying the surface of silica particles so that the particles can be dispersed in the organic solvents. As the organic solvent, the use of chloroform is particularly suitable.

The surface modification can be conducted in various ways, one of which can be practiced through the following procedures. First, the solution of silica particles as synthe sized above is reacted with EDC/NHS materials, which are mainly used to act as the chemical catalyst, and aminobenzothiol (ABT), which is the material having amine group and thiol group, under applying the ultrasound to prepare silica particles in which ABT is fixed on the surface thereof. In this manner, the solution of silica particles uniformly dispersed in the organic solvent, i.e. the solution of silica particles, of which the surface is modified with the short organic molecule having a thiol group, uniformly dispersed in the phase of the organic solvent can thus be prepared.

Next, the dispersed solution of ABT-fixed silica particles is washed with ethanol and chloroform through the centrifuge procedure to prepare the silica nanoparticle-dispersed solution having a certain size for the Langmuir-Blodgett procedure. The use of such process is desirable from the aspects that the reaction procedures are relatively simple and further, as describes above, silica having various particle sizes can be synthe sized by controlling the concentration of TEOS and ammonia water and the reaction conditions.

According to this, using said silica particle-dispersed solution the single layer film of silica particles of which the surface is modified with the organic functional groups can be prepared on the basis of the Langmuir-Blodgett method (Step S22). One example of the procedures of the step (S22) will be more specifically illustrated.

First, the silica particle-dispersed solution prepared in the above step (S20) is spread on the water surface, wherein said silica particle-dispersed solution is in the state that silica particles modified at the surface thereof with the organic molecule having a thiol group are uniformly dispersed in chloroform. At this time, the barrier is placed on said water surface and then moved in the direction that silica particles are gathered together, to gradually reduce the silica particle-floating area thereby allowing silica particles to gather in the form of a thin film. In this procedure, the structure of the silica film can be controlled by altering the arrangement state of silica particles and the film forming state with the surface pressure. The pressure applied to the barrier is designated as the transition pressure. The present inventors have found that when this pressure is 35 mN/m-45 mN/m, the uniform layer in which neither empty void nor multi-layer of silica particles is formed can be produced.

Next, silica particles in the form of the thin film, which is uniformly arranged on the water surface, are attached to the gold substrate by fixing the said substrate to a dipper and then raising up the substrate. Here, it should be noted that when unmodified silica particles are dispersed in the organic solvent and then spread on the water surface, the particles may either form the non-uniform thin film or precipitated in water due to the interaction between the surface of particles and the water surface, whereas the solution of silica particles of which the surface is modified with the organic functional group can form the very uniform, single-layer thin film. The gold substrate can be formed by flatly depositing gold on the cover glass with a certain thickness, for example, a thickness of 20 to 100 nanometers, by means of the vacuum vapor deposition.

Figure 4:
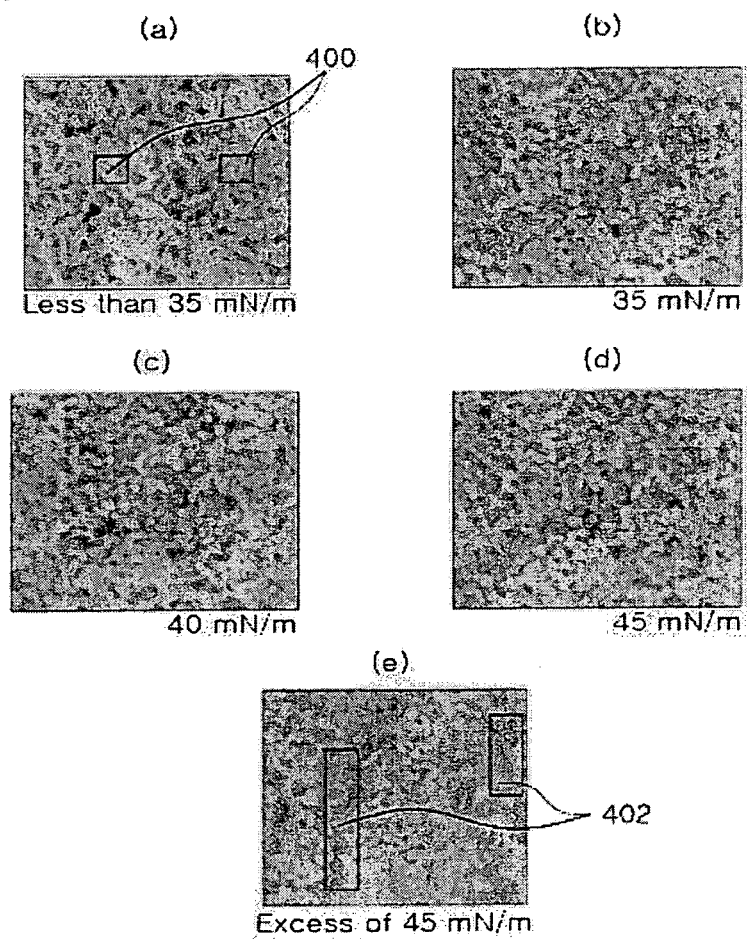
FIG. 4 is a scanning electron microscopic photograph to show the transferred state of silica particles depending on the transition pressure.
Figure 5:
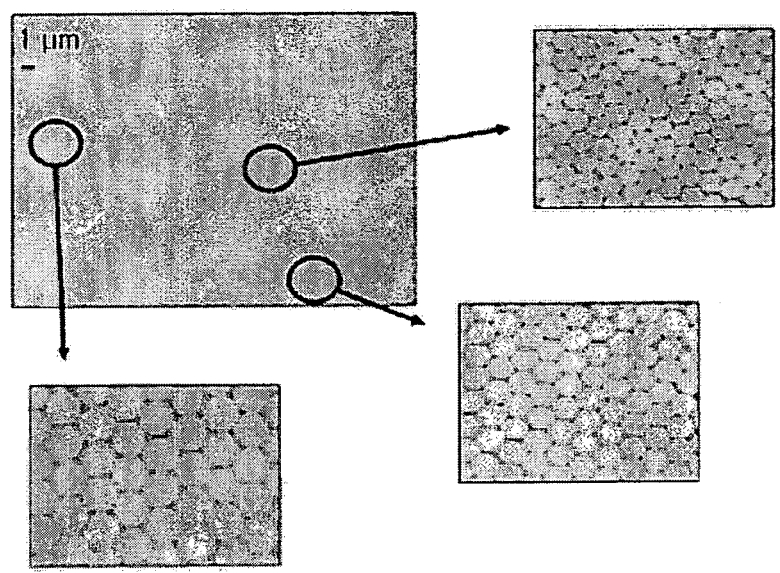
FIG. 5 is a scanning electron microscopic photograph to show the transferred state of silica particles well-established as a tight, single-layer.

In this connection, FIG. 4 is a photograph to show the transferred state of silica particles depending on the transition pressure as obtained by the scanning electron microscopy (SEM). With referring to (a) of FIG. 4, at the transition pressure less than 35 mM/m, e.g. 30 mM/m the empty voids (400) having no silica particles are generated. With referring to (b), (c) and (d) of FIG. 4, it can be seen that at an out 35-45 mM/m silica particles are transferred to the substrate in the form of the single-layer thin film in which the particles have a void-free, uniform two-dimensional crystalline form. In addition, with referring to (e) of FIG. 4, at the pressure in excess of 45 mM/m, for example, at 50 mM/m the single-layer silica film is destroyed at some area to produce a portion forming the irregular, multi-layer (402). FIG. 4(c) shows the scanning electron microscopic photograph to present the transferred state of silica particles well-established as a tight, single-layer.

Next, another gold thin film is again established on the gold substrate to which the silica particle LB thin film is transferred, by means of the vacuum vapor deposition, for example, the electron-beam evaporation (Step S24). More specifically, this step is the step for transferring silica particles having a particle size of about 300 nm diameter on the gold substrate produced as shown above, by means of LB method. In order to systemically control the size and shape of the nanostructures formed on the gold substrate, and the distance between said structures, etc., the size of silica particles used can be controlled to different sizes, for example as 100, 130, 300 and 500 nm, in addition to the particle size of about 300 nm.

Figure 6:
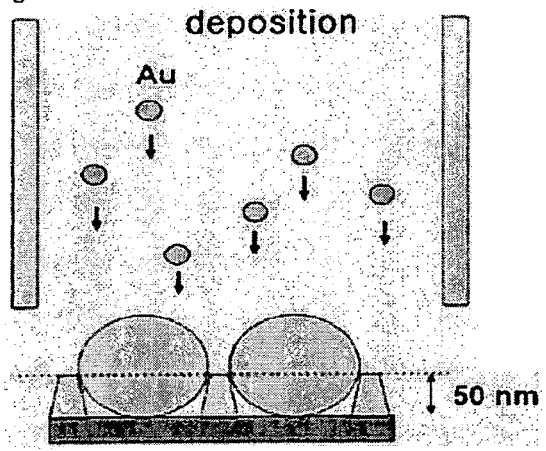
FIG. 6 is a schematic diagram to illustrate the procedures of the vapor deposition.
Figure 7:
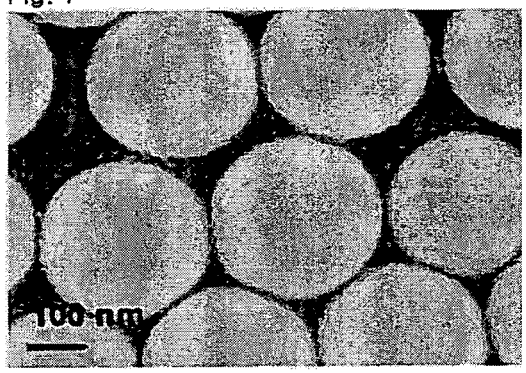
FIG. 7 is a scanning electron microscopic photograph after vapor deposition of gold.

In order to establish the gold thin film, the electrochemical reduction may be used. However, such electrochemical reduction has the problems that some impurities may be incorporated and further, that the manufacturing procedures are complicated. Therefore, according to the examples of the present invention, the method wherein gold serves as a source of evaporation and said evaporated gold atom is deposited on the pre-prepared silica particle LB thin film is used as the dry-type, film-forming technology of which the procedures are simple and which has little concern of contamination. For this technology, the electron-beam evaporation is preferably used as the vacuum vapor deposition. FIG. 6 is the schematic diagram to illustrate the procedures of the vapor deposition. When using the plasma-mode ion deposition, it is not easy to form the lithographic pattern on a nano-scale since the inert gas for generating plasma is present in the chamber and thus, ionized gold particles are deposited while scattering and spreading due to collision of said gold particles with gas. On the contrary, the vapor deposition using electron beam cumulatively deposits gold particles without collision with gas, and therefore, is desirable for forming the lithographic pattern on a silica scale. FIG. 7 shows the photograph obtained by the scanning electron microscopy after vapor deposition of gold. With referring to FIG. 7, it can be seen that it is possible to clearly observe the photograph at a higher magnification in the state that gold as the conductive metal is deposited.

Then, silica particles are removed by ultrasound treatment to manufacture the gold structure with silica structure (Step S26). In case where silica particles are to be removed, the gold thin film is formed again on the silica particle-transferred substrate to the thickness of 20 nm, 50 nm and 100 nm by using the electron beam evaporation, and then, the resulting substrate is washed in the ultrasonic wave washer containing ethanol to remove silica particles thereby preparing the substrate on which the nanostructure formed with gold is formed. This step can be excluded since the substrate from which silica particles are not removed can also be sued as the template.

Figure 8:
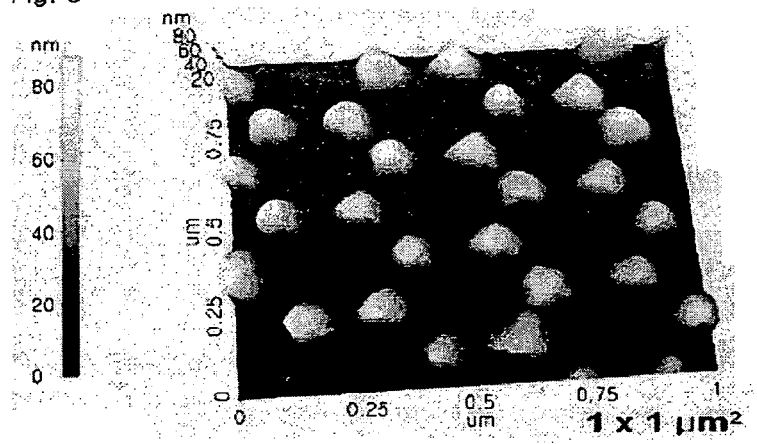
FIG. 8 shows the results obtained by taking the photograph of surface of the gold structure deposited in the manner of the vacuum vapor deposition according to the example of the present invention, with the Atomic Force Microscopy (AFM)
Figure 9:
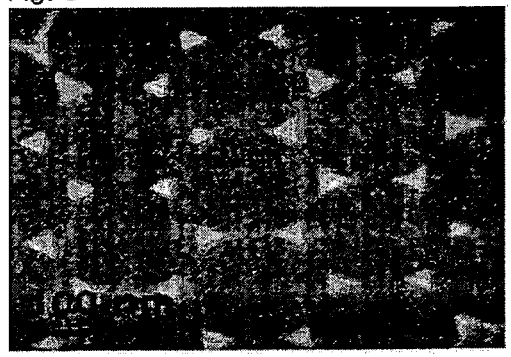
FIG. 9 shows the results obtained by taking the photograph of surface of the gold structure deposited by the electron beam mode according to the example of the present invention, with the Scanning Electron Microscopy (SEM)
Figure 10:
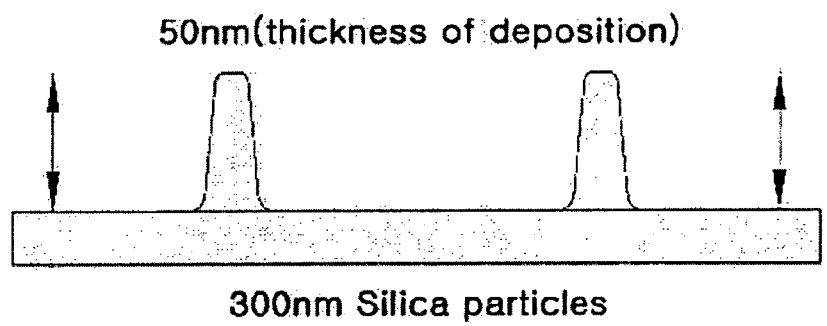
FIG. 10 is a schematic diagram showing the sectional view of the gold structure deposited by the electron beam mode according to the example of the present invention.

FIGS. 8 and 9 show the results obtained by taking the photographs of surface of the gold structure deposited by the electron beam mode according to the example of the present invention, with the Atomic Force Microscopy (AFM) and the Scanning Electron Microscopy (SEM), respectively. In addition, FIG. 10 is the schematic diagram showing the sectional view of the gold structure deposited by the electron beam mode according to the example of the present invention. With referring FIGS. 8 and 9, it could be identified that upon using the electron beam evaporation, since gold particles are entered into the gap between silica particles without collision with gas molecules, gold highly builds up only in the gap between silica particles and thus, it is possible to produce the analytical sensor in a mass scale by manufacturing the substrate having a great area, which is uniform in view of the size, distance and orientation of particles, under various deposition conditions.

Figure 11:
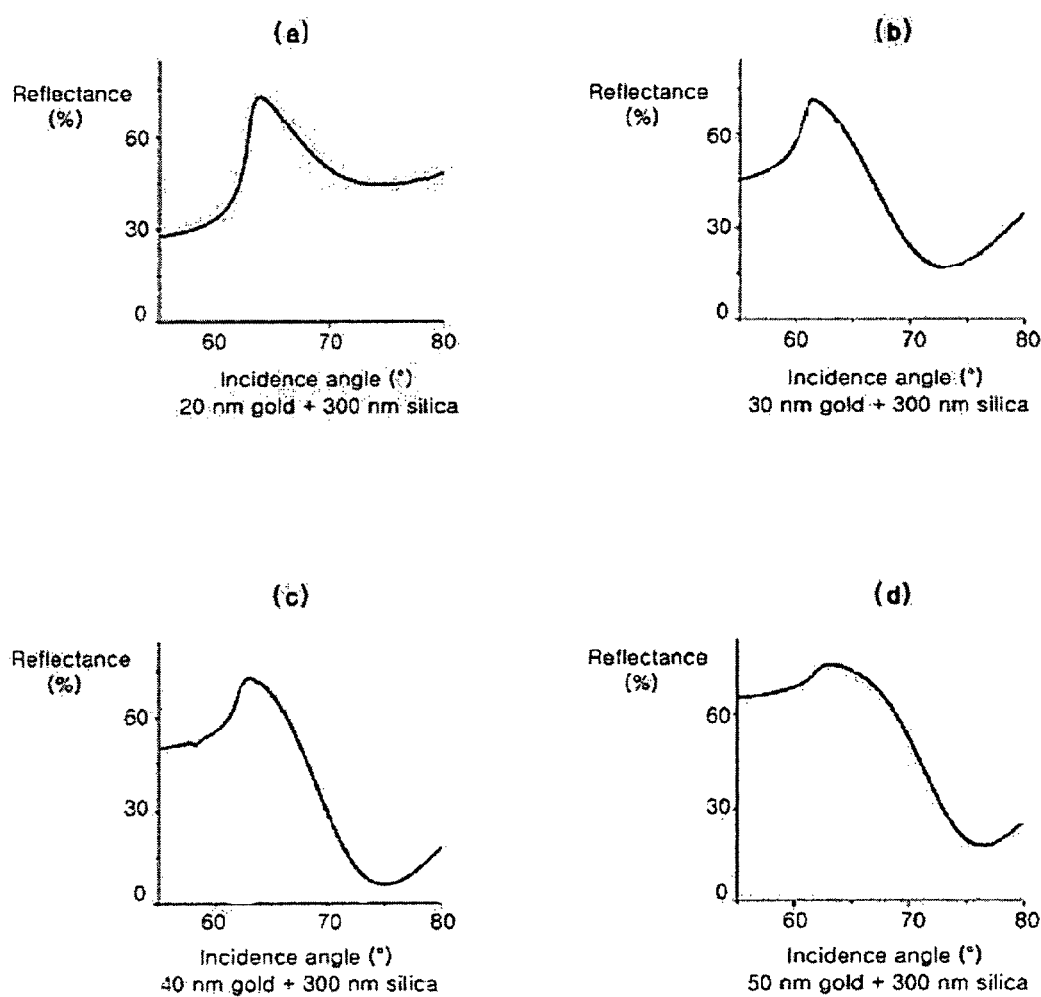
FIGS. 11 and 12 are the graphs showing the resonance curves of SPR depending on a change in thickness of the bottom gold layer in cases where gold is deposited to the thickness of 20 nm and 50 nm.
Figure 12:
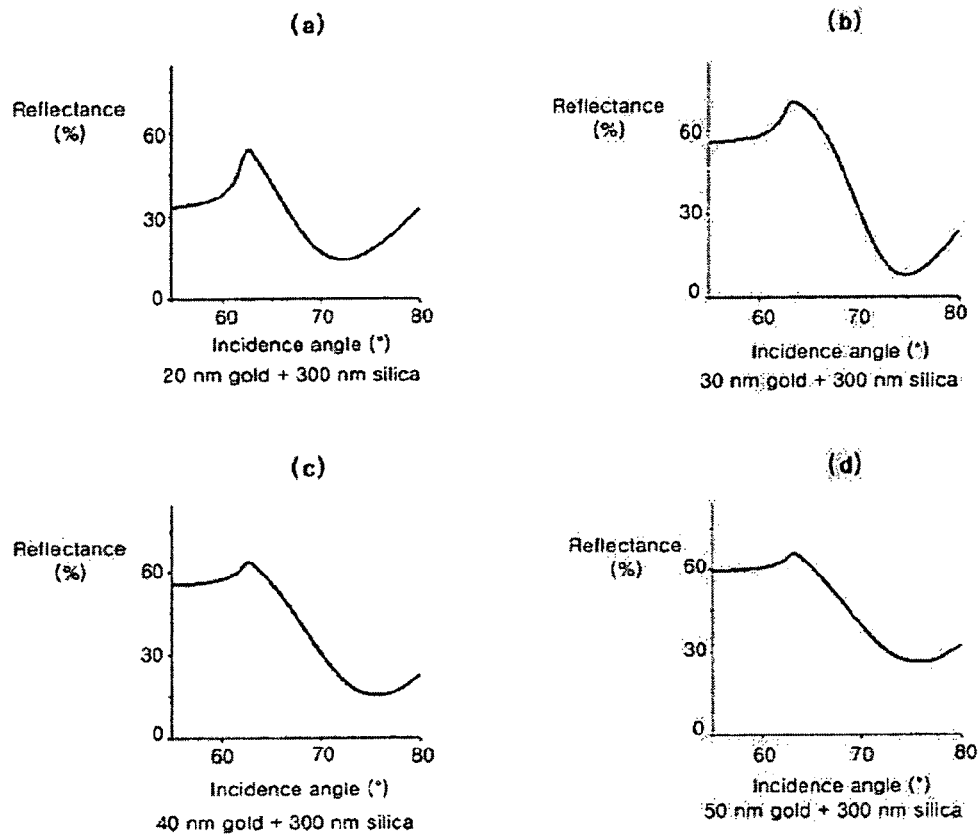

Then, the substrate on which the gold silica structure manufactured according to the above method is formed was fitted on SPR equipment and distilled water was added thereto to measure the SPR signal. FIGS. 11 and 12 show the resonance curve of SPR depending on a change in thickness of the bottom gold layer in cases where gold is deposited to the thickness of 20 nm and 50 nm. With referring to FIGS. 11 and 12, it can be seen that in cases where gold is deposited to the thickness of 20 nm and 50 nm the resonance curve of SPR is varied depending on a change in thickness of the bottom gold layer. In addition, it is confirmed that all the substrates having the bottom thickness of 30, 40 and 50 nm sufficiently show the SPR curve form, and an improvement in the sensitivity was measured through the aqueous ethanol solution.

Figure 13:
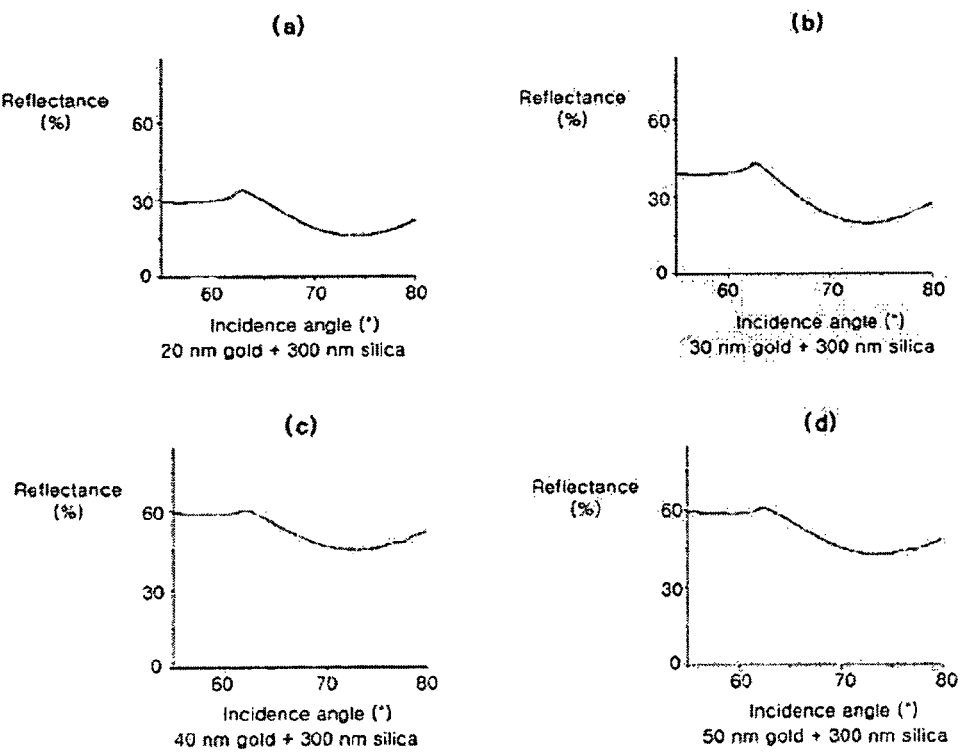
FIG. 13 is the graph showing the resonance curve of SPR depending on a change in thickness of the bottom gold layer in cases where gold is deposited to the thickness of 100 nm.

FIG. 13 shows the resonance curve of SPR depending on a change in thickness of the bottom gold layer in cases where gold is deposited to the thickness of 100 nm. With referring to FIG. 13, in case where the gold thin film is again deposited to the thickness of 100 nm, SPR curve does not show for the substrates having all the thickness of the bottom gold layer. Accordingly, it is desirable that the gold thin layer is formed to the thickness less than 100 nm.

Figure 14:
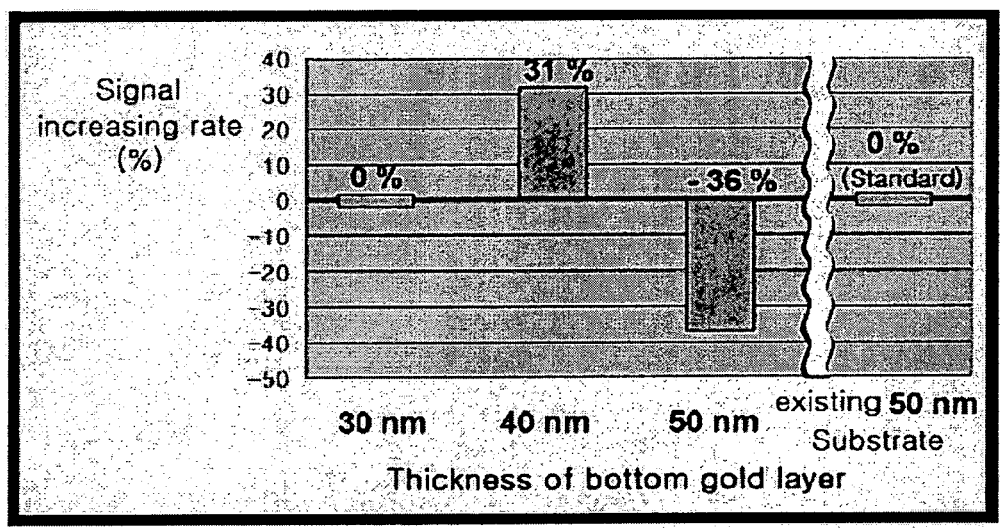
FIG. 14 is the graph showing the results obtained by measuring the ratio of SPR sensitivity by the thickness of the bottom gold as compared to the silica structure substrate deposited to the thickness of 50 nm.
Figure 15:
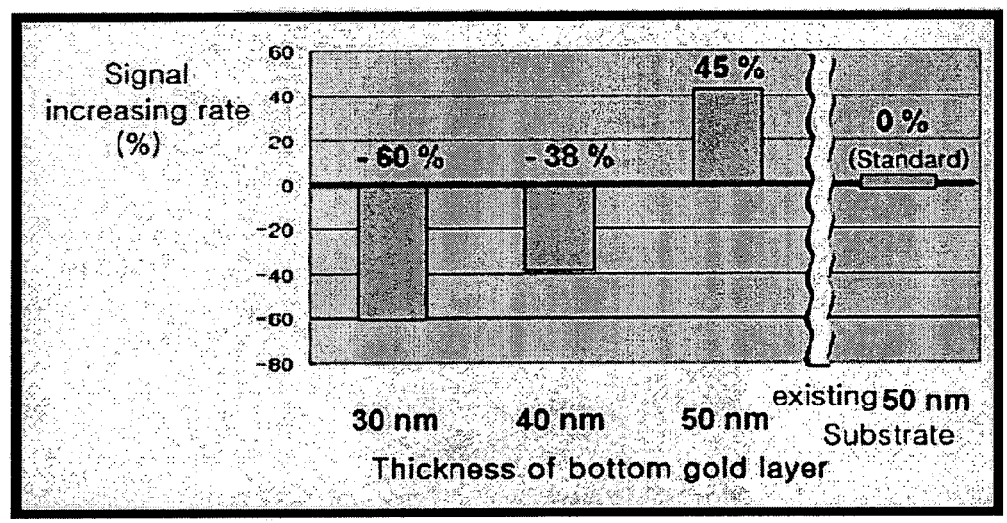
FIG. 15 is the graph showing the results obtained by measuring the ratio of SPR sensitivity by the thickness of the bottom gold as compared to the silica structure substrate deposited to the thickness of 20 nm.

The results obtained from comparison of the shifts of the resonance angle depending on a difference in the refractive indices of the silica structure substrates manufactured by again depositing gold having the thickness of 20 nm and 50 nm on the gold substrate on which silica particle LB thin film is transferred, through SPR using distilled water and 20% (w/v) aqueous ethanol solution are shown in FIGS. 14 and 15. The horizontal lines shown in FIGS. 14 and 15 indicate the results obtained by measuring SPR values for the bottom gold layer having the thickness of 50 nm, which uses silica nanoparticles as the template and does not deposit the gold nanostructure thereon, and the change ratio of signals is determined as being 0%.

In case where the 300 nm silica particle LB thin film is used as the template and gold is deposited to the thickness of 50 nm thereon, the improvement in signals was assessed in comparison to the prior SPR substrate having the thickness of 50 nm. In FIG. 14, the results obtained by measuring the ratio of SPR sensitivity by the thickness of the bottom gold as compared to the silica structure substrate deposited to the thickness of 50 nm are shown as the graph. With referring to FIG. 14, in case where the gold nanostructure is manufactured using silica LB thin film as the template, only the substrate having the bottom thickness of 40 nm shows an increase of signals by about 31% but the signal sensitivity is rather lowered under the remaining conditions.

Then, using the 300 nm silica particle LB thin film as the template an improvement in signals under the conditions of the substrate deposited with gold to the thickness of 20 mm was assessed. In FIG. 15, the results obtained by measuring the ratio of SPR sensitivity by the thickness of the bottom gold as compared to the silica structure substrate deposited to the thickness of 20 nm are shown as the graph. In comparison to the results of FIG. 14, it could be identified that the signals are improved when gold is deposited to the thickness of 20 nm. According to the results shown in FIGS. 14 and 15, it could be noted that under the conditions of the substrates deposited with gold to the thickness of 20 nm using the 300 nm silica particle LB thin film as the template the effect of enhancing the signals is high. Among them, the substrate deposited with gold to the thickness of 20 nm using the 300 nm silica particle LB thin film as the template, with the 50 nm bottom gold thickness shows an increase of signals to the extent of about 45%, and it could be found that such substrate is the condition to provide the highest improvement of signals, through comparison to a change in SPR curve of the prior SPR gold substrate in distilled water and 20% (w/v) aqueous ethanol solution.

INDUSTRIAL APPLICABILITY

According to the present invention, the nanoparticles, which are uniform with respect to the distance between particles, interval and arrangement, can be fixed on the solid substrate having a great area above 10×10 cm$^3$ using the Langmuir-Blodgett method. The nanofilm thus produced can be used as the substrate of the analytical sensor, and when the analytical sensitivity property is measured using the substrate of the analytical sensor thus prepared it could be identified that the sensitivity can be highly improved.

The invention claimed is:

1. A method for manufacturing a substrate of an analytical sensor, said method comprising:
   (a) the step of preparing a dispersed solution of nanoparticles by surface-modifying said nanoparticles with an organic functional group and dispersing such surface-modified nanoparticles in a volatile organic solvent;
   (b) the step of preparing a single layer film of the nanoparticles surface-modified with said organic functional group using said dispersed solution of nanoparticles on the basis of the Langmuir-Blodgett method, and then transferring said single layer film of nanoparticles to the substrate;
   (c) the step of coating the substrate to which said single layer film of nanoparticles is transferred, with a metal thin film by means of vacuum vapor deposition; and
   (d) the step of removing nanoparticles after coating with the metal thin film by means of the vacuum vapor deposition.

2. The method for manufacturing the substrate of the analytical sensor according to claim 1, wherein said nanoparticles are silica particles.

3. The method for manufacturing the substrate of the analytical sensor according to claim 1, wherein said organic functional group is a thiol group.

4. The method for manufacturing the substrate of the analytical sensor according to claim 1, wherein said organic solvent is chloroform.

5. The method for manufacturing the substrate of the analytical sensor according to claim 1, wherein said metal thin film is a gold thin film.

6. The method for manufacturing the substrate of the analytical sensor according to claim 1, wherein said vacuum vapor deposition is the electron beam evaporation.

7. The method for manufacturing the substrate of the analytical sensor according to claim 2, wherein said silica particles in said step (a) is prepared by self-assembly of tetraethylorthosilicate (TEOS), an organic molecule comprising silicon, using ammonia water as a catalyst.

8. The method for manufacturing the substrate of the analytical sensor according to claim 1, wherein said step (a) comprises:
   (a-1) the step of preparing silica particles by self-assembly of the organic molecule comprising silicon, tetraethylorthosilicate (TEOS), using ammonia water as a catalyst; and
   (a-2) the step of centrifuging silica particles as prepared in said step (a-1) by means of a centrifuge, immersing the particles, discarding the supernatant, and then drying the particles for a baking time at a certain temperature above the phase transition temperature to prepare silica particles;
   (a-3) the step of reacting EDC/NHS materials with aminobenzothiol (ABT), as the material having an amine group and a thiol group, under ultrasound application to fix ABT on the surface of silica particles, thereby preparing the dispersed solution of ABT-fixed silica particles; and
   (a-4) the step of washing the dispersed solution of ABT-fixed silica particles as prepared in said step (a-3) with ethanol and chloroform through the centrifuge procedure to prepared the solution to be used in the Langmuir-Blodgett method, thereby surface-modifying silica particles.

9. The method for manufacturing the substrate of the analytical sensor according to claim 1, wherein said step (b) comprises:
   (b-1) the step of spreading the dispersed solution of silica nanoparticles, which are surface-modified with the organic molecule having the organic functional groups and dispersed in the organic solvent, on the water surface;
   (b-2) the step of placing a barrier on said water surface to allow silica particles to gather as the form of the thin film; and
   (b-3) the step of transferring silica particles in the form of the thin film to the gold substrate.

10. The method for manufacturing the substrate of the analytical sensor according to claim 9, wherein the transition pressure applied to said barrier is 35-45 mN/m.

11. The method for manufacturing the substrate of the analytical sensor according to claim 8, wherein said nanoparticles are silica particles.

12. The method for manufacturing the substrate of the analytical sensor according to claim 8, wherein said organic functional group is a thiol group.

13. The method for manufacturing the substrate of the analytical sensor according to claim 8, wherein said organic solvent is chloroform.

* * * * *